(12) United States Patent
Lee et al.

(10) Patent No.: US 8,410,203 B2
(45) Date of Patent: Apr. 2, 2013

(54) PHOSPHORUS COMPOUND, METHOD OF PREPARING THE SAME AND FLAME RETARDANT THERMOPLASTIC RESIN COMPOSITION INCLUDING THE SAME

(75) Inventors: Min Soo Lee, Uiwang-si (KR); Im Hyuck Bae, Uiwang-si (KR); Seon Ae Lee, Uiwang-si (KR); Sang Hyun Hong, Uiwang-si (KR); Chang Hong Ko, Uiwang-si (KR); Boem Jun Joo, Uiwang-si (KR); Jin Hwan Kim, Suwon-si (KR); Ik Hyun Yu, Suwon-si (KR); Thi Hai Vo, Suwon-si (KR); Thanh Kieu Giang, Suwon-si (KR); Thi Thuy Hang Nguyen, Suwon-si (KR)

(73) Assignee: Cheil Industries Inc., Gumi-si (KR)

( * ) Notice: Subject to any disclaimer, the term of this patent is extended or adjusted under 35 U.S.C. 154(b) by 0 days.

(21) Appl. No.: 13/271,742

(22) Filed: Oct. 12, 2011

(65) Prior Publication Data
US 2012/0165444 A1    Jun. 28, 2012

(30) Foreign Application Priority Data
Dec. 22, 2010  (KR) .......... 10-2010-0132902
Mar. 29, 2011  (KR) .......... 10-2011-0028418

(51) Int. Cl.
*C08K 5/523*    (2006.01)
(52) U.S. Cl. ............... 524/127; 558/97; 558/162
(58) Field of Classification Search ........ 524/127; 558/97, 162
See application file for complete search history.

(56) References Cited

U.S. PATENT DOCUMENTS

| | | | |
|---|---|---|---|
| 5,420,327 A | 5/1995 | Bright et al. | |
| 2002/0065343 A1* | 5/2002 | Jang et al. | 524/127 |
| 2002/0137824 A1* | 9/2002 | Hong et al. | 524/136 |
| 2006/0183825 A1* | 8/2006 | Ahn et al. | 524/117 |
| 2006/0183826 A1* | 8/2006 | Ryu et al. | 524/117 |
| 2006/0183827 A1* | 8/2006 | Jin et al. | 524/117 |
| 2006/0189729 A1* | 8/2006 | Bae et al. | 524/117 |
| 2006/0189730 A1* | 8/2006 | Hong et al. | 524/117 |
| 2007/0155872 A1* | 7/2007 | Hong et al. | 524/115 |
| 2007/0155875 A1* | 7/2007 | Ku et al. | 524/117 |

FOREIGN PATENT DOCUMENTS

| | | |
|---|---|---|
| EP | 0509506 A2 | 10/1992 |
| GB | 2325933 A | 12/1998 |
| JP | 1991-211293 | 9/1991 |
| JP | 08208972 | 8/1996 |
| WO | 2005012417 A1 | 2/2005 |
| WO | 2005017030 A1 | 2/2005 |

OTHER PUBLICATIONS

European Search Report in counterpart European Application No. 11185963.3 dated Apr. 17, 2012, pp. 1-4.

* cited by examiner

*Primary Examiner* — Peter Szekely
(74) *Attorney, Agent, or Firm* — Summa, Additon & Ashe, P.A.

(57) ABSTRACT

Disclosed herein is a phosphorus compound represented by Formula 1:

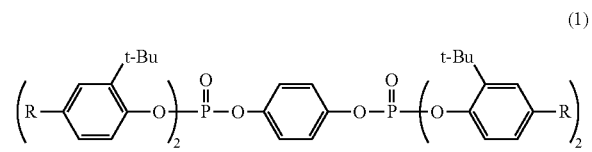

(1)

wherein each R is the same or different and is independently hydrogen, $C_1$-$C_6$ alkyl or $C_6$-$C_{12}$ aryl.

10 Claims, 1 Drawing Sheet

PHOSPHORUS COMPOUND, METHOD OF PREPARING THE SAME AND FLAME RETARDANT THERMOPLASTIC RESIN COMPOSITION INCLUDING THE SAME

CROSS-REFERENCE TO RELATED APPLICATIONS

This application claims priority under 35 USC Section 119 to and the benefit of Korean Patent Application No. 10-2010-0132902 filed Dec. 22, 2010, and Korean Patent Application No. 10-2011-0028418 filed Mar. 29, 2011, the entire disclosure of each of which is incorporated herein by reference.

1. Field of the Invention

The present invention relates to a novel phosphorus compound, a method of preparing the same, and a flame retardant thermoplastic resin composition including the same.

2. Description of the Related Art

In recent years, plastic polymers and synthetic resins have been widely used in a variety of applications, including vehicles, construction materials, aircraft, railroads and home appliances. In addition, the rapid development of various kinds of functional additives has lead to an explosive increase in the types of applications for plastic polymers and synthetic resins.

Plastics are easily combustible because of their inherent characteristics and have no resistance to fire. Accordingly, plastics can combust when exposed to external ignition sources and can allow fire to propagate faster. In view of this, governmental agencies in many countries, including the United States, Japan and Europe, have enacted laws and regulations requiring that polymeric resins meet flame retardancy standards to guarantee the safety of electronic products against fire.

Many methods are known to impart flame retardancy to polymers. Such methods include, for example, synthesis of thermally stable resins via molecular structure design, chemical modification of conventional polymers (reactive type), physical addition of flame retardants by blending or compounding (additive type), and coating or painting with flame retardants. The addition of flame retardants to polymeric resins is widely used to impart flame retardancy to resins. Additive type flame retardants are classified as halogen, phosphorus, nitrogen, silicon and inorganic flame retardants, depending on their constituent components.

Halogen flame retardants react with gas-phase radicals generated during combustion of polymers to inhibit chain reactions of combustion. Typical halogen flame retardants are polybromodiphenyl ether, tetrabromobisphenol A, brominated epoxy compounds and chlorinated polyethylene.

Brominated flame retardants are most widely used in electrical and electronic fields due to their outstanding physical properties, low prices and superior flame retardancy. However, environmental problems associated with the use of brominated flame retardants remain controversial, and the Restriction of Hazardous Substances (RoHS) Directive bans the use of many brominated flame retardants (called deca) in electrical and electronic products. Since then, the use of brominated flame retardants used has drastically dropped.

Phosphorus flame retardants have emerged as representative environmentally friendly non-halogen flame retardants that are capable of complying with recent environmental regulations. Such phosphorus flame retardants exhibit excellent flame retardant effects in solid-phase reactions and are particularly effective in plastics containing a large amount of oxygen. Examples of phosphorus flame retardants include phosphates, phosphine oxides, phosphites, and phosphonates flame retardants, among others. Aromatic phosphoric acid esters, such as resorcinol bisphenol phosphate and bisphenol bisdiphenyl phosphate, are commonly used at present.

The use of phosphorus flame retardants can improve flame retardancy and increase the flowability of resins, which are advantageous in terms of ease of processing. Phosphorous flame retardants, however, can deteriorate the heat resistance of resins.

As the application of synthetic resins has been extended to vehicles, aircraft, and the like, and the degree of integration of electronic materials has increased, there is an increasing need for highly heat resistant resins. Conventional phosphoric acid ester flame retardants cause many problems during processing, such as gas evolution, degradation and poor appearance, because of their low heat resistance.

Japanese Patent No. 1991-211293 is directed to a flame retardant having a structure in which resorcinol linking two phosphate moieties is substituted with hydroquinone or biphenol. However, there is little increase in thermal deformation temperature and hydrolysis tends to occur.

United Kingdom Patent No. 2325933 reports a flame retardant in which 2, 4-di-tert-butylphenol groups are introduced to achieve improved heat resistance and impact strength while maintaining good flame retardancy. However, the complicated synthesis of the flame retardant limits the practical application of the same. It was also found that the flame retardant does not substantially contribute to improvements of flame retardancy and heat resistance, causes poor flowability, and readily undergoes hydrolysis.

The present inventors have developed novel phosphorus compounds that can be more easily synthesized and that can exhibit improved flame retardancy, heat resistance, impact strength and hydrolysis resistance without deteriorated flowability, as compared to conventional phosphorus compounds. The present inventors also have developed environmentally friendly flame retardant thermoplastic resin compositions that can have superior heat resistance and impact strength while also possessing good flame retardancy, and which can exhibit reduced or minimal problems during processing, such as gas evolution, degradation and poor appearance.

SUMMARY OF THE INVENTION

The present invention provides a phosphorus compound that can have improved thermal stability and hydrolysis resistance compared to conventional aromatic phosphoric acid esters, can exhibit superior flame retardancy, heat resistance and impact strength without deteriorating flowability, can minimize or eliminate problems during processing, such as gas evolution, degradation and poor appearance, is environmentally friendly because it does not release halogenated gases, can possess improved hydrolysis resistance, and can achieve a good balance of physical properties, such as flame retardancy, impact strength, resistance, flowability and hydrolysis resistance, when used with a thermoplastic resin. The present invention also provides a thermoplastic resin composition using the phosphorus compound that can find application in electrical/electronic fields and as a molded material for vehicles, aircraft, and the like due to its excellent flame retardancy, hydrolysis resistance and heat resistance.

More particularly, the present invention relates to a novel phosphorus compound including phenol moieties, each having a tert-butyl group in a particular position of the phenol ring, and a hydroquinone linker to achieve improved flame retardancy, heat resistance and impact strength, a method of preparing the phosphorus compound, and a flame retardant thermoplastic resin composition including the phosphorus compound. In exemplary embodiments, the phosphorus compound is represented by Formula 1:

[Formula 1]

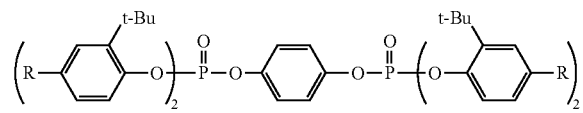
(1)

wherein each R is the same or different and is independently hydrogen, $C_1$-$C_6$ alkyl or $C_6$-$C_{12}$ aryl.

In exemplary embodiments, the difference in the acid value of a 75% solution of the phosphorus compound in water before and after stirring at 93° C. for 48 hours may be less than about 0.5 mg KOH/g, and the difference in the acid value of the phosphorus compound before and after standing at 280° C. for 1 hour may be less than about 0.1 mg KOH/g.

The phosphorus compound may have a weight loss of about 5.5% or less, as determined by thermogravimetric analysis at 350° C.

The present invention also provides a method of preparing the phosphorus compound. In exemplary embodiments, the phosphorus compound may be prepared by the reaction of phosphorus oxychloride, hydroquinone and a compound represented by Formula 2:

[Formula 2]

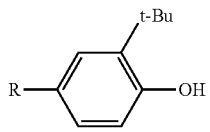
(2)

wherein R is hydrogen, $C_1$-$C_6$ alkyl or $C_6$-$C_{12}$ aryl.

In an alternative embodiment, the method may include reacting phosphorus oxychloride with the compound of Formula 2 and reacting the reaction product with hydroquinone.

The phosphorus compound can exhibit excellent flame retardancy, heat resistance and impact strength, and thus is suitable for use as a flame retardant for a thermoplastic resin.

The present invention also provides a flame retardant thermoplastic resin composition including the phosphorus compound of Formula 1. In exemplary embodiments, the thermoplastic resin composition may include about 100 parts by weight of a thermoplastic resin and about 0.1 to about 50 parts by weight of the phosphorus compound of Formula 1.

Examples of thermoplastic resins suitable for use in the thermoplastic resin composition may include without limitation polystyrene (PS) resins, acrylonitrile-butadiene-styrene (ABS) copolymer resins, rubber modified polystyrene (HIPS) resins, acrylonitrile-styrene-acrylate (ASA) copolymer resins, acrylonitrile-styrene (SAN) copolymer resins, methyl methacrylate-butadiene-styrene (MBS) copolymer resins, acrylonitrile-ethyl acrylate-styrene (AES) copolymer resins, polycarbonate (PC) resins, polyphenylene ether (PPE) resins, polyphenylene sulfide (PPS) resins, polyethylene (PE) resins, polypropylene (PP) resins, polyethylene terephthalate (PET) resins, polybutylene terephthalate (PBT) resins, poly (meth)acrylic resins, polyamide (PA) resins and the like, and combinations thereof.

In exemplary embodiments, the thermoplastic resin may be a polycarbonate resin. In this embodiment, the phosphorus compound may be included in an amount of about 1 to about 10 parts by weight, based on about 100 parts by weight of the polycarbonate resin.

In an alternative embodiment, the thermoplastic resin may be a blend of a polycarbonate resin and a rubber modified aromatic vinyl polymer resin. In this embodiment, the phosphorus compound may be included in an amount of about 10 to about 25 parts by weight, based on about 100 parts by weight of the blend.

The thermoplastic resin composition may further include one or more additives selected from the group consisting of flame retardants, flame retardant assistants, lubricants, plasticizers, heat stabilizers, anti-drip agents, antioxidants, compatibilizers, light stabilizers, pigments, dyes, inorganic additives, and combinations thereof.

DETAILED DESCRIPTION OF THE INVENTION

Figure 1:
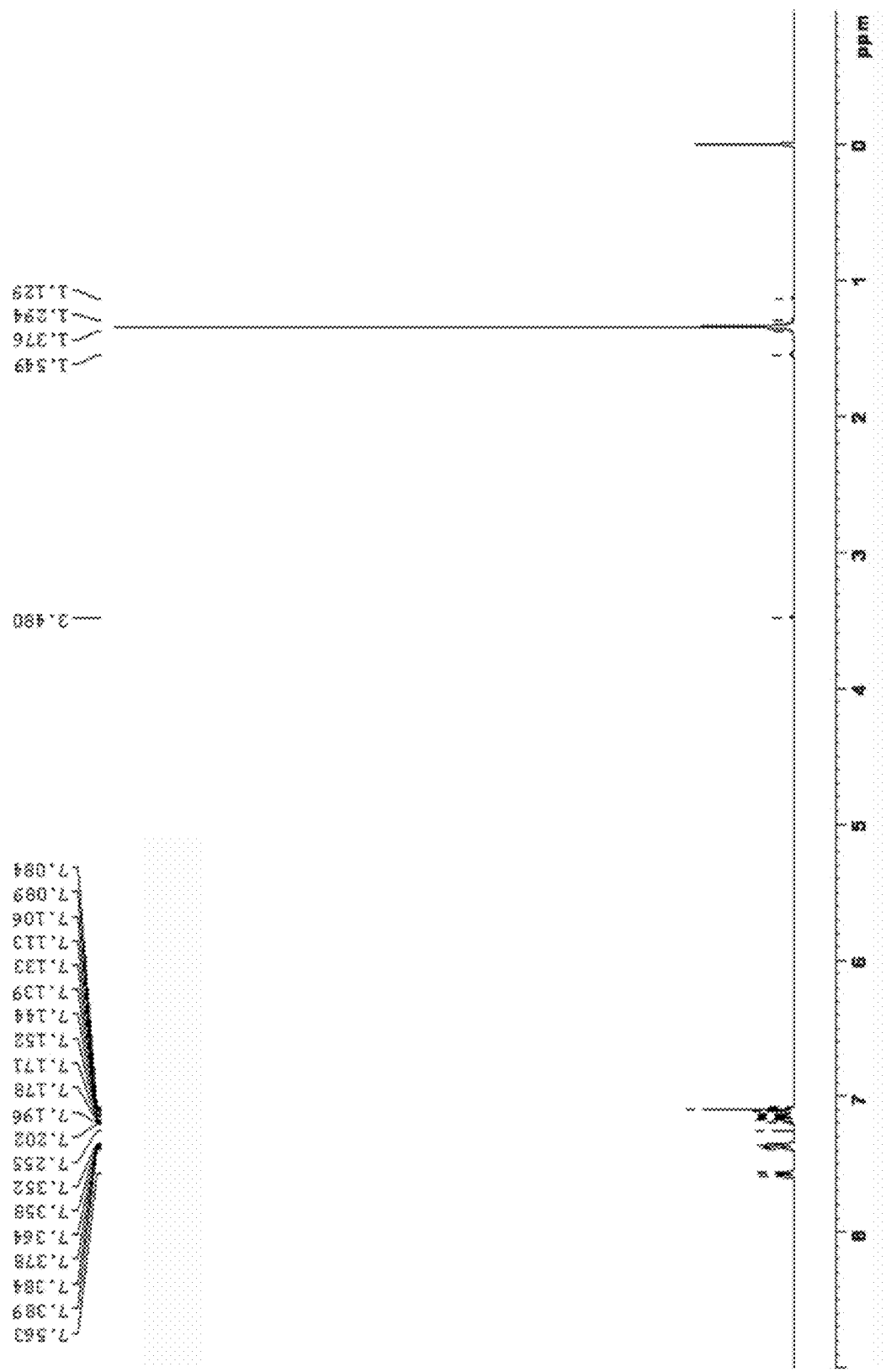
FIG. 1 is an H-NMR spectrum of a phosphorus compound prepared in Example 1.

The present invention now will be described more fully hereinafter in the following detailed description of the invention with reference to the accompanying drawings, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The present invention provides a phosphorus compound represented by Formula

[Formula 1]

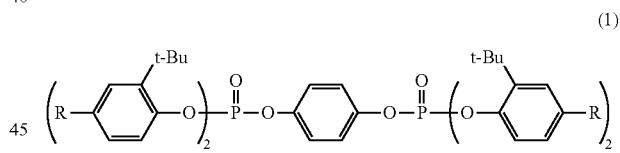
(1)

wherein each R is the same or different and is independently hydrogen, $C_1$-$C_6$ alkyl or $C_6$-$C_{12}$ aryl.

In exemplary embodiments, in Formula 1, each R can be hydrogen or linear alkyl, for example hydrogen, methyl or ethyl, and as another example hydrogen.

The phosphorus compound is characterized by the introduction of tert-butyl groups in the ortho positions of the phenol rings and the presence of a hydroquinone linker. The introduction of tert-butyl groups in the ortho positions can offer superior flame retardancy, heat resistance and hydrolysis resistance, compared to the introduction of tert-butyl groups in the 2,4-, 2,6-, 2,4,6-, 2,3,5,6-, 3,5-, 4- and 2,3,4,5,6-positions.

In the case of a flame retardant having alkyl groups, such as methyl, ethyl, propyl or n-butyl groups, other than t-butyl groups introduced in the ortho positions of the phenol rings, sufficient flame retardancy cannot be achieved. In this case, the flame retardant may also be volatile during processing and good hydrolysis resistance of the flame retardant is difficult to obtain.

The difference in the acid value of a 75% solution of the phosphorus compound in water before and after stirring at 93° C. for 48 hours is less than about 0.5 mg KOH/g, for example less than about 0.3 mg KOH/g, and as another example, from about 0.01 to about 0.25 mg KOH/g.

The acid value is measured by dissolving about 0.5 to about 20 g of the sample in 50 ml of dimethyl sulfoxide, adding about 1 to about 2 ml of a BTB solution thereto and titrating the resulting mixture with an about 0.1 N NaOH solution, and is calculated by the following equation:

Acid value=((Amount (ml) of 0.1N NaOH solution consumed)*(0.1N NaOH solution factor)*5.61)/ Sample amount (g)

The difference in the acid value of the phosphorus compound before and after standing at 280° C. for 1 hour is less than about 0.1 mg KOH/g, for example less than about 0.05 mg KOH/g, and as another example, from about 0 to about 0.01 mg KOH/g.

The phosphorus compound can have a weight loss of about 5.5% or less, for example from 0.1 to 5%, and as another example from 0.1 to 3%, as determined by thermogravimetric analysis at 350° C.

The phosphorus compound may be prepared by the reaction of phosphorus oxychloride, hydroquinone and a compound represented by Formula 2:

[Formula 2]

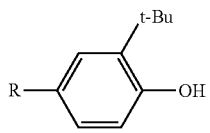

(2)

wherein R is hydrogen, $C_1$-$C_6$ alkyl or $C_6$-$C_{12}$ aryl.

In an alternative embodiment, the method may include reacting phosphorus oxychloride with the compound of Formula 2 and reacting the reaction product with hydroquinone.

For example, the method may include reacting phosphorus oxychloride with 2-tert-butylphenol to prepare di-2-tert-butylphenyl chlorophosphate and reacting the di-2-tert-butylphenyl chlorophosphate with hydroquinone.

In exemplary embodiments, the reaction between the phosphorus chloride compound and the tert-butylphenol may be carried out in the presence of a Lewis acid catalyst or a base catalyst.

The Lewis acid catalyst may be a metal chloride or oxide. Examples of such metal chlorides may include, but are not necessarily limited to, magnesium chloride, aluminum chloride, calcium chloride, and the like, and combinations thereof. The Lewis acid catalyst is used in an amount of about 0.1 to about 10 mol %, for example about 0.5 to about 5 mol %, and as another example about 1 to about 2 mol %. Using the Lewis acid catalyst in an amount within this range can increase the reaction rate and can allow ready removal after reaction.

The base catalyst is an organic amine compound. Examples of the organic amine compounds may include without limitation aromatic amines, such as pyridine and lutidine, and tertiary amines, such as trialkylamine. In exemplary embodiments, the organic amine can be pyridine or triethylamine. The amount of the base catalyst used can be from about 1 to about 3 equivalents, for example from about 1.1 to about 2 equivalents, and as another example from about 1.2 to about 1.5 equivalents, relative to the amount of the chlorine elements of the raw material. Given the equivalent ratio, the completeness of the reaction can be increased while minimizing the formation of by-products.

A solvent can be used for the reaction. The solvent may be an aprotic organic solvent that has a boiling point of about 110 to about 200° C. and does not possess a hydroxyl group. Examples of aprotic organic solvents may include without limitation aromatic compounds, such as toluene, xylene, chlorobenzene and dichlorobenzene. These solvents may be used alone or as a mixture of two or more thereof. In exemplary embodiments, the solvent can be toluene, xylene or chlorobenzene. A solvent having a boiling point lower than about 110° C. can make the reaction rate very slow. Meanwhile, a solvent having a boiling point higher than about 200° C. may not be completely removed by drying after reaction and disadvantageously can cause a color change of the reaction product.

The phosphorus chloride compound may be reacted with the tert-butylphenol compound at a temperature of about 80 to about 170° C., for example about 100 to about 160° C.

The reaction between the phosphorus chloride compound and the tert-butylphenol compound yields a tert-butylphenyl chlorophosphate compound as an intermediate. Thereafter, hydroquinone is added to and reacted with the intermediate. The hydroquinone can be used in an amount of about 0.5 to about 2 equivalents with respect to about 1 equivalent of the phosphorus chloride compound. Given the equivalent ratio, the completeness of the reaction can be increased while minimizing the formation of by-products.

The phosphorus compound can exhibit excellent flame retardancy, hydrolysis resistance, heat resistance and impact strength, and thus can be suitable for use as a flame retardant for a thermoplastic resin, such as an oxygen-containing thermoplastic resin.

The present invention also provides a flame retardant thermoplastic resin composition including the phosphorus compound. The thermoplastic resin composition may include about 100 parts by weight of a thermoplastic resin and about 0.1 to about 50 parts by weight of the phosphorus compound. In some embodiments, the thermoplastic resin composition may include the phosphorous compound in an amount of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 parts by weight. Further, according to some embodiments of the present invention, the amount of the phosphorous compound can be in a range from about any of the foregoing amounts to about any other of the foregoing amounts.

The thermoplastic resin composition may achieve a Flame retardancy of V-1 or V-0 at a thickness of 1.5 mm, as determined by the UL-94 vertical test, and may have a thermal deformation temperature of at least about 90° C., for example about 90.5 to about 135° C.

Examples of thermoplastic resins suitable for use in the thermoplastic resin composition may include, but are not limited to, aromatic vinyl resins, (meth)acrylate resins, polyolefin resins, polyester resins, polyamide resins, polyvinyl chloride resins, polyphenylene ether (PPE) resins, polyphenylene sulfide (PPS) resins, polycarbonate resins, and the like, and combinations thereof. Examples of the thermoplastic resin may include, but are not necessarily limited to, polystyrene (PS) resins, acrylonitrile-butadiene-styrene (ABS) copolymer resins, rubber modified polystyrene (HIPS) resins, acrylonitrile-styrene-acrylate (ASA) copolymer resins, acrylonitrile-styrene (SAN) copolymer resins, methyl methacrylate-butadiene-styrene (MBS) copolymer resins, acrylonitrile-ethyl acrylate-styrene (AES) copolymer resins, polycarbonate (PC) resins, polyphenylene ether (PPE) resins, polyphenylene sulfide (PPS) resins, polyethylene (PE) resins, polypropylene (PP) resins, polyethylene terephthalate (PET) resins, polybutylene terephthalate (PBT) resins, poly(meth) acrylic resins, polyamide (PA) resins, and the like, and combinations thereof. These thermoplastic resins may be used alone or as a mixture of two or more thereof.

In exemplary embodiments, the thermoplastic resin may be a polycarbonate resin. When the polycarbonate resin is used as a base resin, the thermoplastic resin composition may include about 100 parts by weight of the polycarbonate resin and about 1 to about 10 parts by weight, for example about 3 to about 6 parts by weight, of the phosphorus compound. In some embodiments, the thermoplastic resin composition may include the phosphorous compound in an amount of about 1, 2, 3, 4, 5, 6, 7, 8, 9, or 10 parts by weight. Further, according to some embodiments of the present invention, the amount of the phosphorous compound can be in a range from about any of the foregoing amounts to about any other of the foregoing amounts.

In an alternative embodiment, the thermoplastic resin may be a blend of a polycarbonate resin and a rubber modified aromatic vinyl polymer resin (for example a rubber modified styrenic polymer resin). In some embodiments, the thermoplastic resin comprises about 1~99% by weight of the polycarbonate resin and about 99~1% by weight of the rubber modified aromatic vinyl polymer resin. When the blend is used as a base resin, the thermoplastic resin composition may include about 100 parts by weight of the blend and about 10 to about 25 parts by weight, for example about 10 to about 20 parts by weight, of the phosphorus compound. In some embodiments, the thermoplastic resin composition may include the phosphorous compound in an amount of about 10, 11, 12, 13, 14, 15, 16, 17, 18, 19, 20, 21, 22, 23, 24, or 25 parts by weight. Further, according to some embodiments of the present invention, the amount of the phosphorous compound can be in a range from about any of the foregoing amounts to about any other of the foregoing amounts.

The thermoplastic resin composition may further include one or more additives according to intended applications. Examples of additives suitable for use in the thermoplastic resin composition include, but are not necessarily limited to, flame retardants, flame retardant assistants, lubricants, plasticizers, heat stabilizers, anti-drip agents, antioxidants, compatibilizers, light stabilizers, pigments, dyes, and inorganic additives. These additives may be used alone or as a mixture of two or more thereof. In exemplary embodiments, the inorganic additives may include without limitation asbestos, glass fibers, talc, ceramics, sulfates, and the like, and combinations thereof. The additives may be used in a total amount of about 30 parts by weight or less, based on about 100 parts by weight of the base resin.

The flame retardants and the flame retardant assistants can be added for the purpose of improving the flame retardancy of the thermoplastic resin composition. The flame retardants and the flame retardant assistants may be any conventional flame retardants and flame retardant assistants known in the art, for example, halogen-containing organic compounds, cyanurate compounds, metal salts, fluorinated polyolefin resins, and the like, and combinations thereof.

Examples of metal salts suitable for use as the flame retardant assistants include without limitation sulfonic acid metal salts and sulfone sulfonic acid metal salts, which are commonly known in the art. Examples of fluorinated polyolefin resins suitable for use as the anti-drip agents may include without limitation polytetrafluoroethylene, polyvinylidene fluoride, tetrafluoroethylene/vinylidene fluoride copolymers, tetrafluoroethylene/hexafluoropropylene copolymers, ethylene/tetrafluoroethylene copolymers, and the like, and combinations thereof. These polyolefin resins may be used either individually or in combination of two or more kinds thereof.

The flame retardant thermoplastic resin composition may be prepared by any suitable method known in the art. For example, the flame retardant thermoplastic resin composition may be prepared by mixing the constituent components and the optional additives simultaneously, and melt-extruding the mixture in an extruder to produce pellets or chips.

The thermoplastic resin composition can have excellent physical properties in terms of flame retardancy and heat resistance. Due to these advantages, the thermoplastic resin composition can be widely used for the production of, for example, housings of electrical and electronic appliances, such as TVs, audio devices, mobile phones, digital cameras, navigation systems, washing machines, computers, monitors, MP3 players, video players, CD players and washers, and other large-sized injection molded articles, such as office automation devices.

There is no particular restriction on the molding method of the thermoplastic resin composition for the production of a plastic molded article. The molding method may be, for example, extrusion, injection molding or casting. The thermoplastic resin composition can easily be molded by those skilled in the art to which the invention pertains.

Hereinafter, the constitution and functions of the present invention will be explained in more detail with reference to the following examples. These examples are provided for illustrative purposes only and are not to be in any way construed as limiting the present invention.

A description of details apparent to those skilled in the art will be omitted.

EXAMPLES

Example 1

2 equivalents of phosphorus oxychloride (Aldrich), 4 equivalents of 2-t-butylphenol (Aldrich) and 4.4 equivalents of triethylamine are added to toluene (in an amount of 10 times that of the phosphorus oxychloride) in a reactor. The mixture is reacted by heating to 130° C. with stirring for at least 10 hr. After completion of the reaction, the reaction mixture is allowed to cool to room temperature. To the reaction mixture are added 1 equivalent of hydroquinone, 2.2 equivalents of triethylamine and toluene (in an amount of one half of the amount initially added), all of which are purchased from Samchun Chemical (Korea). The reactor is heated to 130° C., followed by stirring for at least 10 hr. After the reaction is finished, the reaction mixture is allowed to cool to room temperature and washed three times with water (in an amount of one half of the total amount of the toluene added). The aqueous layer is discarded and the organic solvent is removed under reduced pressure. The residue is completely dissolved in methanol as a recrystallization solvent by heating to 70° C. and is then cooled to 0° C. or less. Filtration afforded a phosphorus compound as a white solid in a yield of 97%. The phosphorus compound is confirmed to have the structure of Formula 1-1 by H-NMR spectroscopy (300 MHz, Bruker). The H-NMR spectrum is shown in FIG. 1.

[Formula 1-1]

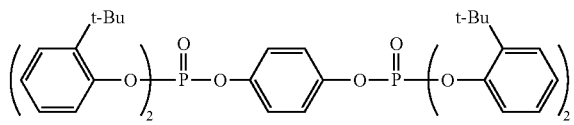

(1-1)

The hydrolysis resistance and heat resistance of the phosphorus compound are evaluated by the following methods:

(1) Hydrolysis resistance: 75 g of the phosphorus compound is dissolved in 25 g of distilled water. The acid values (mg KOH/g) of the solution before and after stirring at 93° C. for 48 hr are compared. For the measurement of acid value, 0.5-20 g of the sample is dissolved in dimethyl sulfoxide (50 ml), 1-2 ml of a BTB solution is added thereto, and the resulting mixture is titrated with a 0.1 N NaOH solution. The acid value is calculated by the following equation:

Acid value=((Amount (ml) of 0.1N NaOH solution consumed)*(0.1N NaOH solution factor)*5.61)/ Sample amount (g)

(2) Heat Resistance:

(a) The heat resistance of the phosphorus compound is evaluated by comparing the acid values of 10 g of the phosphorus compound before and after standing at 280° C. for 1 hr. The acid values are calculated in accordance with the same method as described above.

(b) The weight losses (%) of the phosphorus compound are determined by thermogravimetric analysis at 200° C., 250° C., 300° C. and 350° C.

Comparative Example 1

The hydrolysis resistance and heat resistance of bisphenol bisdiphenyl phosphate (BDP, Yoke (China)) are evaluated by the same methods as described in Example 1.

Comparative Example 2

The hydrolysis resistance and heat resistance of PX-200 (Daihachi, Japan) are evaluated by the same methods as described in Example 1.

TABLE 1

|  |  | Example 1 | Comparative Example 1 | Comparative Example 2 |
|---|---|---|---|---|
| Hydrolysis resistance (Acid value difference: mg KOH/g) |  | 0.24 | 0.91 | 2.20 |
| Heat resistance (Acid value difference: mg KOH/g) |  | 0.00 | 0.89 | 1.19 |
| Weight losses (%) | 200° C. | 0.6 | 1.0 | 0.4 |
|  | 250° C. | 0.6 | 1.6 | 0.7 |
|  | 300° C. | 1.3 | 4.1 | 4.2 |
|  | 350° C. | 4.9 | 17.6 | 19.5 |

Example 2

5 parts by weight of the phosphorus compound of Formula 1-1 and about 100 parts by weight of a bisphenol A type polycarbonate (PANLITE L-1250W, Teijin (Japan)) having a weight average molecular weight of 25,000 g/mol are extruded using a general twin-screw extruder to produce pellets. The pellets are dried at 80° C. for 2 hr and molded using a 10 oz injection molding machine at 200-280° C. to produce a specimen. The mold temperature is 40-80° C.

Comparative Example 3

A specimen is produced in the same manner as in Example 2, except that PX-200 (Daihachi, Japan) is used instead of the phosphorus compound.

TABLE 2

|  | Example 2 | Comparative Example 3 |
|---|---|---|
| Flame retardancy(UL94, ⅛") | V-0 | V-1 |
| Heat resistance rating (VST, ° C.) | 130.4 | 128.1 |
| IZOD (⅛", kgf · cm/cm) | 13.2 | 11.4 |

* VST (Vicat softening temperature) is measured in accordance with ISO R 306. A 5 kg weight is used.
* IZOD (kgf · cm/cm) is measured at a thickness of ⅛" in accordance with ASTM D-256.

As can be seen from the results in Table 2, the specimen using the phosphorus compound (Example 2) exhibits significantly improved flame retardancy, heat resistance and impact strength compared to the specimen using the compound PX-200 (Comparative Example 3).

Examples 3-6

The procedure of Example 1 is repeated, except that the phosphorus compound of Formula 1-1 and a blend of a bisphenol A type polycarbonate (PANLITE L-1250W, Teijin (Japan)) having a weight average molecular weight of 25,000 g/mol and a rubber reinforced styrene resin (CHT, Cheil Industries Inc. (Korea)) as a base resin are mixed in accordance with the compositions shown in Table 3.

TABLE 3

|  | Examples | | | |
|---|---|---|---|---|
|  | 3 | 4 | 5 | 6 |
| Polycarbonate resin | 80 | 80 | 80 | 80 |
| Rubber reinforced aromatic vinyl polymer | 20 | 20 | 20 | 20 |
| Phosphorus compound of Formula 1-1 | 12 | 14 | 16 | 18 |
| Flame retardancy(UL94, 2 mm) | V-0 | V-0 | V-0 | V-0 |
| Flame retardancy(UL94, 1.5 mm) | V-1 | V-0 | V-0 | V-0 |
| Heat resistance rating (HDT, ° C.) | 96.2 | 93.2 | 91.2 | 90.6 |

Comparative Examples 4-7

The procedure of Examples 3-6 is repeated, except that bisphenol bisdiphenyl phosphate (BDP, Yoke (China)) is used instead of the phosphorus compound of Formula 1-1. The results are shown in Table 4.

TABLE 4

|  | Comparative Examples | | | |
|---|---|---|---|---|
|  | 4 | 5 | 6 | 7 |
| Polycarbonate resin | 80 | 80 | 80 | 80 |
| Rubber reinforced aromatic vinyl polymer | 20 | 20 | 20 | 20 |
| Phosphorus compound (BDP) | 12 | 14 | 16 | 18 |
| Flame retardancy(UL94, 2 mm) | V-0 | V-0 | V-0 | V-0 |
| Flame retardancy(UL94, 1.5 mm) | V-2 | V-1 | V-0 | V-0 |
| Heat resistance rating (HDT, ° C.) | 92.5 | 87.7 | 84.2 | 81.5 |

Comparative Examples 8-11

The procedure of Examples 3-6 is repeated, except that PX-200 (Daihachi, Japan) is used instead of the phosphorus compound of Formula 1-1. The results are shown in Table 5.

TABLE 5

|  | Comparative Examples | | | |
|---|---|---|---|---|
|  | 8 | 9 | 10 | 11 |
| Polycarbonate resin | 80 | 80 | 80 | 80 |
| Rubber reinforced aromatic vinyl polymer | 20 | 20 | 20 | 20 |
| Phosphorus compound (BDP) | 12 | 14 | 16 | 18 |
| Flame retardancy (UL94, 2 mm) | V-0 | V-0 | V-0 | V-0 |
| Flame retardancy (UL94, 1.5 mm) | V-1 | V-0 | V-0 | V-0 |
| Heat resistance (HDT, ° C.) | 90.6 | 87.2 | 85.2 | 83.2 |

As can be seen from the results in Tables 3-5, despite the use of the rubber reinforced aromatic vinyl polymer, the compositions of Examples 3-6 including the phosphorus compound of Formula 1-1 have better heat resistance and flame retardancy than those of Comparative Examples 4-11.

Methods for Evaluation of Physical Properties (1) Flame retardancy is evaluated on 2 mm and 1.5 mm thick specimens by the UL-94 vertical test.

(2) Heat resistance is evaluated by measuring heat distortion temperature (HDT) in accordance with ASTM D648 (¼", 18.5 kgf/cm$^2$, 120° C./hr).

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A phosphorus compound represented by Formula 1:

[Formula 1]

$$\left(R-\underset{t\text{-}Bu}{\underset{|}{\text{C}_6H_3}}-O\right)_2 \overset{O}{\underset{\|}{P}}-O-\text{C}_6H_4-O-\overset{O}{\underset{\|}{P}}\left(O-\underset{t\text{-}Bu}{\underset{|}{\text{C}_6H_3}}-R\right)_2$$

wherein each R is hydrogen.

2. The phosphorus compound of claim 1, wherein the difference in the acid value of a 75% solution of the phosphorus compound in water before and after stirring at 93° C. for 48 hours is less than about 0.5 mg KOH/g, and the difference in the acid value of the phosphorus compound before and after standing at 280° C. for 1 hour is less than about 0.1 mg KOH/g.

3. The phosphorus compound of claim 1, wherein said phosphorus compound has a weight loss of about 5.5% or less, as determined by thermogravimetric analysis at 350° C.

4. A method of preparing a phosphorus compound represented by Formula 1:

[Formula 1]

$$\left(R-\underset{t\text{-}Bu}{\underset{|}{\text{C}_6H_3}}-O\right)_2 \overset{O}{\underset{\|}{P}}-O-\text{C}_6H_4-O-\overset{O}{\underset{\|}{P}}\left(O-\underset{t\text{-}Bu}{\underset{|}{\text{C}_6H_3}}-R\right)_2$$

wherein each R is hydrogen, the method comprising reacting phosphorus oxychloride with a compound represented by Formula 2:

[Formula 2]

$$R-\underset{t\text{-}Bu}{\underset{|}{\text{C}_6H_3}}-OH$$

wherein R is hydrogen, and
reacting the reaction product with hydroquinone.

5. A flame retardant thermoplastic resin composition comprising the phosphorus compound of claim 1.

6. The flame retardant thermoplastic resin composition of claim 5, wherein said thermoplastic resin composition comprises about 100 parts by weight of a thermoplastic resin and about 0.1 to about 50 parts by weight of the phosphorus compound.

7. The flame retardant thermoplastic resin composition of claim 5, wherein said thermoplastic resin comprises polystyrene (PS) resin, acrylonitrile-butadiene-styrene (ABS) copolymer resin, rubber modified polystyrene (HIPS) resin, acrylonitrile-styrene-acrylate (ASA) copolymer resin, acrylonitrile-styrene (SAN) copolymer resin, methyl methacrylate-butadiene-styrene (MBS) copolymer resin, acrylonitrile-ethyl acrylate-styrene (AES) copolymer resin, polycarbonate (PC) resin, polyphenylene ether (PPE) resin, polyphenylene sulfide (PPS) resin, polyethylene (PE) resin, polypropylene (PP) resin, polyethylene terephthalate (PET) resin, polybutylene terephthalate (PBT) resin, poly(meth)acrylic resin, polyamide (PA) resin, or a combination thereof.

8. The flame retardant thermoplastic resin composition of claim 5, wherein the thermoplastic resin is polycarbonate resin and wherein said phosphorus compound is present in an amount of about 1 to about 10 parts by weight, based on about 100 parts by weight of the polycarbonate resin.

9. The flame retardant thermoplastic resin composition of claim 5, wherein the thermoplastic resin is a blend of a polycarbonate resin and a rubber modified aromatic vinyl polymer resin, and wherein the phosphorus compound is present in an amount of about 10 to about 25 parts by weight, based on about 100 parts by weight of the blend of the polycarbonate resin and the rubber modified aromatic vinyl polymer resin.

10. The flame retardant thermoplastic resin composition of claim 5, further comprising an additive selected from the group consisting of flame retardants, flame retardant assistants, lubricants, plasticizers, heat stabilizers, anti-drip agents, antioxidants, compatibilizers, light stabilizers, pigments, dyes, inorganic additives, and combinations thereof.

* * * * *